(12) United States Patent
Ricke et al.

(10) Patent No.: US 7,970,472 B2
(45) Date of Patent: Jun. 28, 2011

(54) SYSTEM AND METHOD OF DETECTING AND DIAGNOSING PACING SYSTEM MALFUNCTIONS

(75) Inventors: Anthony Ricke, Wauwatosa, WI (US); Gordon Ian Rowlandson, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 505 days.

(21) Appl. No.: 12/144,075

(22) Filed: Jun. 23, 2008

(65) Prior Publication Data
US 2009/0318997 A1 Dec. 24, 2009

(51) Int. Cl.
*A61N 1/00* (2006.01)
(52) U.S. Cl. .......................................... 607/27
(58) Field of Classification Search ............. 607/27
See application file for complete search history.

(56) References Cited

U.S. PATENT DOCUMENTS

| | | | |
|---|---|---|---|
| 4,088,139 A | 5/1978 | Auerbach | |
| 4,142,533 A | 3/1979 | Brownlee et al. | |
| 4,208,008 A * | 6/1980 | Smith | 714/811 |
| 4,291,703 A | 9/1981 | Kelen | |
| 4,527,567 A | 7/1985 | Fischler et al. | |
| 4,532,934 A | 8/1985 | Kelen | |
| 4,574,813 A | 3/1986 | Regan | |
| 4,664,116 A | 5/1987 | Shaya et al. | |
| 4,832,041 A | 5/1989 | Wang et al. | |
| 5,184,615 A | 2/1993 | Nappholz et al. | |
| 5,265,603 A | 11/1993 | Hudrlik | |
| 5,309,919 A | 5/1994 | Snell et al. | |
| 5,601,615 A | 2/1997 | Markowitz et al. | |
| 5,660,183 A | 8/1997 | Chiang et al. | |
| 5,682,902 A | 11/1997 | Herleikson | |
| 5,741,312 A | 4/1998 | Vonk et al. | |
| 5,776,168 A | 7/1998 | Gunderson | |
| 5,861,012 A | 1/1999 | Stroebel | |
| 5,891,179 A | 4/1999 | Er et al. | |
| 5,913,828 A | 6/1999 | Russell | |
| 5,954,754 A | 9/1999 | Stoop et al. | |
| 5,961,468 A | 10/1999 | Emmrich | |
| 6,067,472 A | 5/2000 | Vonk et al. | |

(Continued)

FOREIGN PATENT DOCUMENTS
JP 04097758 A 3/1992
(Continued)

OTHER PUBLICATIONS
GB Search Report dated Oct. 2, 2009.

*Primary Examiner* — George Manuel
(74) *Attorney, Agent, or Firm* — Andrus, Sceales, Starke & Sawall, LLP

(57) ABSTRACT

A method of diagnosing a malfunction of a pacing system includes the steps of receiving a biopotential signal, detecting a pacing system malfunction, detecting a cause of the malfunction, and displaying the detected malfunction and detected cause of the malfunction. A pacing system is also disclosed herein. The system includes an electrode array that receives a biopotential signal associated with the pacing system. A malfunction detector applies a malfunction logic to the biopotential signal to identify a pacing system malfunction and applies a morphology logic to the biopotential signal to identify a morphology of the biopotential signal. An output generator receives an indication of the identified pacing system malfunction and the identified cause of the malfunction and creates an output indicative of the identified pacing system malfunction and the identified cause.

22 Claims, 4 Drawing Sheets

U.S. PATENT DOCUMENTS

| | | |
|---|---|---|
| 6,129,745 A | 10/2000 | Sun et al. |
| 6,167,309 A | 12/2000 | Lyden |
| 6,195,584 B1 | 2/2001 | Hill et al. |
| 6,216,037 B1 | 4/2001 | Van Oort |
| 6,249,702 B1 | 6/2001 | Van Oort |
| 6,351,675 B1 | 2/2002 | Tholen et al. |
| 6,631,293 B2 | 10/2003 | Lyden |
| 6,654,640 B2 | 11/2003 | Lyden |
| 6,668,194 B2 | 12/2003 | VanHout |
| 6,901,291 B2 | 5/2005 | Stoop et al. |
| 6,959,214 B2 | 10/2005 | Pape et al. |
| 6,980,851 B2 | 12/2005 | Zhu et al. |
| 7,085,603 B1 | 8/2006 | Florio et al. |

FOREIGN PATENT DOCUMENTS

| | | |
|---|---|---|
| WO | 2005/101229 A1 | 10/2005 |

* cited by examiner

SYSTEM AND METHOD OF DETECTING AND DIAGNOSING PACING SYSTEM MALFUNCTIONS

BACKGROUND

The present disclosure relates to the field of patient monitoring. More specifically, the present disclosure relates to monitoring the functioning of an implantable device using surface ECG by receiving the surface ECG and producing an analysis of the monitored implantable device function.

Electrical impulses originating in the tissues of the heart cause the heart to cyclically contract. When, due to heart disease or tissue damage, the heart tissue fails to properly create and/or propagate these electrical impulses, an artificial electronic pacemaker may be implanted to provide the necessary stimulation. The design and implementation of an electronic device that is implanted into the body of a patient is a challenging task. The interior of the human body presents a hostile and dynamic environment in which the pacemaker is required to function. Challenges arise to proper pacemaker function both in terms of the constantly moving and changing environment in which the pacemaker must operate, as well as the body's own defensive mechanisms aimed to isolate and destroy any foreign objects.

Studies have found that pacemaker lead fractures can occur at a rate between 0.1% and 4.2% per patient-year. Additionally, atrial and right ventricle dislodgments, on average, occur at a rate of 2.2% per patient-year. Furthermore, left ventricle lead dislodgment, on average, occurs at a rate of 8% per patient-year.

There are three categories of the most common pacemaker complications. These categories include failure to sense, failure to capture, and inappropriate rate. A failure to sense complication is a pacing system malfunction in which the pacemaker fails to properly detect the electrical stimulation of the heart muscle tissue. A failure to capture complication is a pacing system malfunction in which the pacemaker fails to generate a pace pulse with sufficient power to stimulate the myocardium (heart tissue). Inappropriate rate is a pacing system malfunction in which the pacemaker generates the pacing pulses at either too low or too fast of a rate.

Since the pacing system works in conjunction with the heart's own biopotentials, the artificial electronic stimulation of the heart by the pacing system may be detected through the use of an electrocardiogram (ECG). An analysis of the electrical activity in the heart as shown by the ECG can be used to identify whether the pacemaker is properly functioning, or can be used to identify which of the above-referenced complications are being experienced by the pacing system.

While systems for detecting the existence of a pacing system complication or malfunction have been available, these systems have not taken this analysis any further. Therefore, often once a pacing system malfunction has been detected, complicated and time consuming techniques such as chest X-rays and RF communication with the pacemaker must be used to further distinguish the cause of the pacing system malfunction.

BRIEF DESCRIPTION OF THE DISCLOSURE

An embodiment of a method of diagnosing a malfunction of a pacing system is disclosed herein. The method begins with receiving a combined signal. Next, a pacing system malfunction is detected. Then, the cause of the detected malfunction is detected. Finally, the detected malfunction and the detected cause of the malfunction are displayed.

An embodiment of a system for detecting pacing system malfunctions is disclosed herein. The system includes an electrode array configured to be attached to a patient being treated with an electrical pacing system. A malfunction detector includes a malfunction logic and a morphology logic and applies the malfunction logic to the pacer signal to identify a pacing system malfunction and applies the morphology logic to the pacer signal to identify a morphology indicative of the cause of the malfunction. An output generator is connected to the malfunction detector and creates an output that displays the identified pacing system malfunction and the identified cause.

An alternative embodiment of a pacing system is further disclosed herein. The pacing system includes a pacemaker connected to the heart of the patient. An electrode array is attached to the patient at locations suitable for acquisition of a combined signal from the heart and the pacemaker. An ECG monitor is connected to the electrode array and the combined signal acquired by the electrode array is transmitted to the ECG monitor. A malfunction detector applies malfunction logic to the acquired combined signal to identify at least one pacing defect present in the combined signal. The malfunction detector applies morphology logic to the combined signal to identify the morphology of the combined signal. An output generator is connected to the malfunction detector and receives an indication of the determined cause of the malfunction and produces an output indicative of the determined cause.

DETAILED DISCLOSURE

Figure 1:
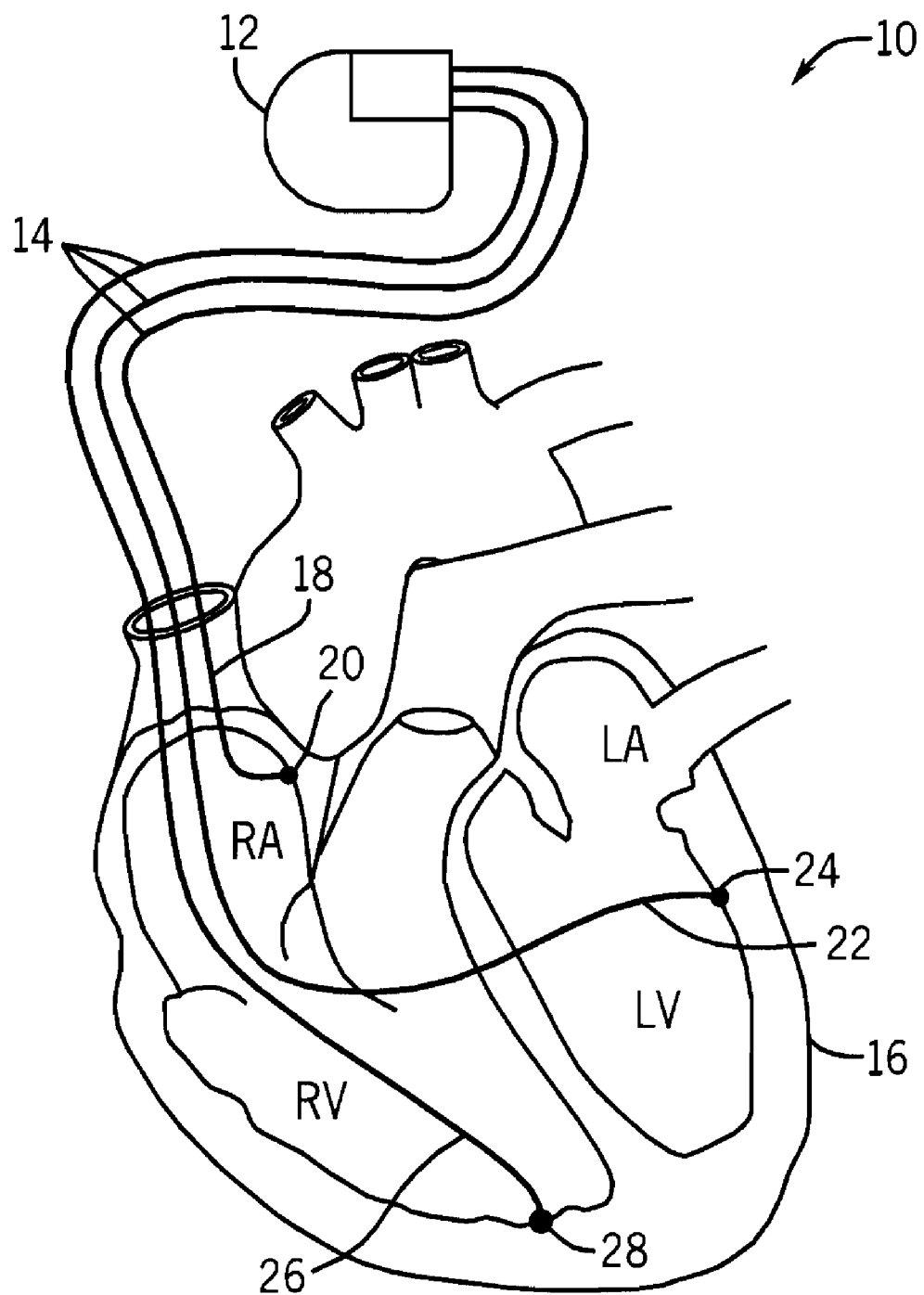
FIG. 1 depicts an embodiment of a pacing system.

FIG. 1 depicts an exemplary embodiment of a pacing system 10 as it appears inside the body of a patient. The pacing system 10 includes an implantable pacemaker 12. A plurality of pacer leads 14 extend from the pacemaker 12. The pacer 12. The pacer leads 14 extend from the pacemaker 12 into the heart 16 of the patient. Each of the pacer leads 14 extends to a different portion of the heart 16 and terminates in a pacer electrode. The RA pacer lead 18 extends to the right atrium (RA) and terminates at an RA pacer electrode 20. The LV pacer lead 22 extends to the left ventricle (LV) and terminates in an LV pacer electrode 24. An RV pacer lead 26 extends to the right ventricle (RV) and terminates at the RV pacer electrode 28.

While these three pacer electrode placements have been herein described, it is understood that pacer electrodes may be positioned at alternative locations on the heart and a patient may be treated using one or more pacer electrodes in a pacing system 10 and need not use, or be limited to, an arrangement with the three pacer electrodes as described above.

The pacer electrodes (20, 24, 28) are attached to the myocardium (muscle tissue) of the heart using a fixation mechanism. In the case of the RA pacer electrode 20 and the RV pacer electrode 28, the fixation mechanism is often a screw-type device that secures the electrode and creates a favorable electrical connection between the pacer electrode and the myocardium. Alternatively, as is used commonly with the LV pacer electrode 24, the electrode is not attached to the myocardium per se, but rather the LV pacer lead 22 is placed in the coronary sinus vein and tension in the LV pacer lead 22, or other elastic properties of the LV pacer lead 22 holds the LV pacer electrode 24 in position. This may be used in an alternative to other fixation mechanisms so as to prevent damage to the tissue or blood vessel wherein the lead and electrode reside.

The pacemaker 12 monitors the electrical activity of the heart 16 and analyzes these biopotential signals in order to detect abnormalities in the morphology and/or timing in the biopotential signals from the heart. Based on the detected abnormalities, the pacemaker 12 can deliver electrical impulses through the pacing leads 14 to one or more of the pacer electrodes (20, 24, 28).

Another challenge facing the optimal performance of the pacing system 10 is that the interior of the patient's body presents a dynamic and hostile environment for foreign objects. The body, and especially the heart 16, is constantly moving and the body's immune system is designed to isolate and destroy any foreign objects, such as an implanted pacing system 10. Therefore, pacing system malfunctions due to damaged and/or incomplete electrical connections are common occurrences. Due to the dynamic conditions within the patient's body, the pacing leads 14 are constantly moving. Further, the body's immune system makes the insulation over the leads brittle over time. These two factors make the leads susceptible to lead fracture. The constant motion of the pacing system 10 further causes the pacer electrodes to be susceptible to micro and macro dislodgement when the fixation mechanism of the electrode pulls away from the heart tissue or is otherwise dislodged from electrical contact with the target physiological placement.

It is desirable to easily detect the existence of a pacing system malfunction, identify the cause of the malfunction, and remedy this cause in order to provide the patient with the proper pacing therapy. A non-limiting list of pacing system malfunctions includes lead fractures, insulation defects, micro dislodgements, macro dislodgements, battery depletion, and pacemaker hardware defects.

The above-listed malfunctions can manifest in a variety of changes exhibited in the morphology of a detected combined signal, comprising a biopotential signal and a pacer signal, collected from one or more surface electrodes (electrocardiogram (ECG)). A non-limiting list of such manifested pacing system complications include a failure to sense, a failure to capture, and an inappropriate rate. A failure to sense occurs when the pacemaker has failed to sense the response of the myocardium to the electrical pacing stimulus. A failure to capture occurs when the pacemaker fails to generate a stimulus impulse sufficient to stimulate the myocardium. An inappropriate rate is characterized by the pacemaker producing a stimulus impulse at too slowly or too quickly of a rate.

Figure 2:
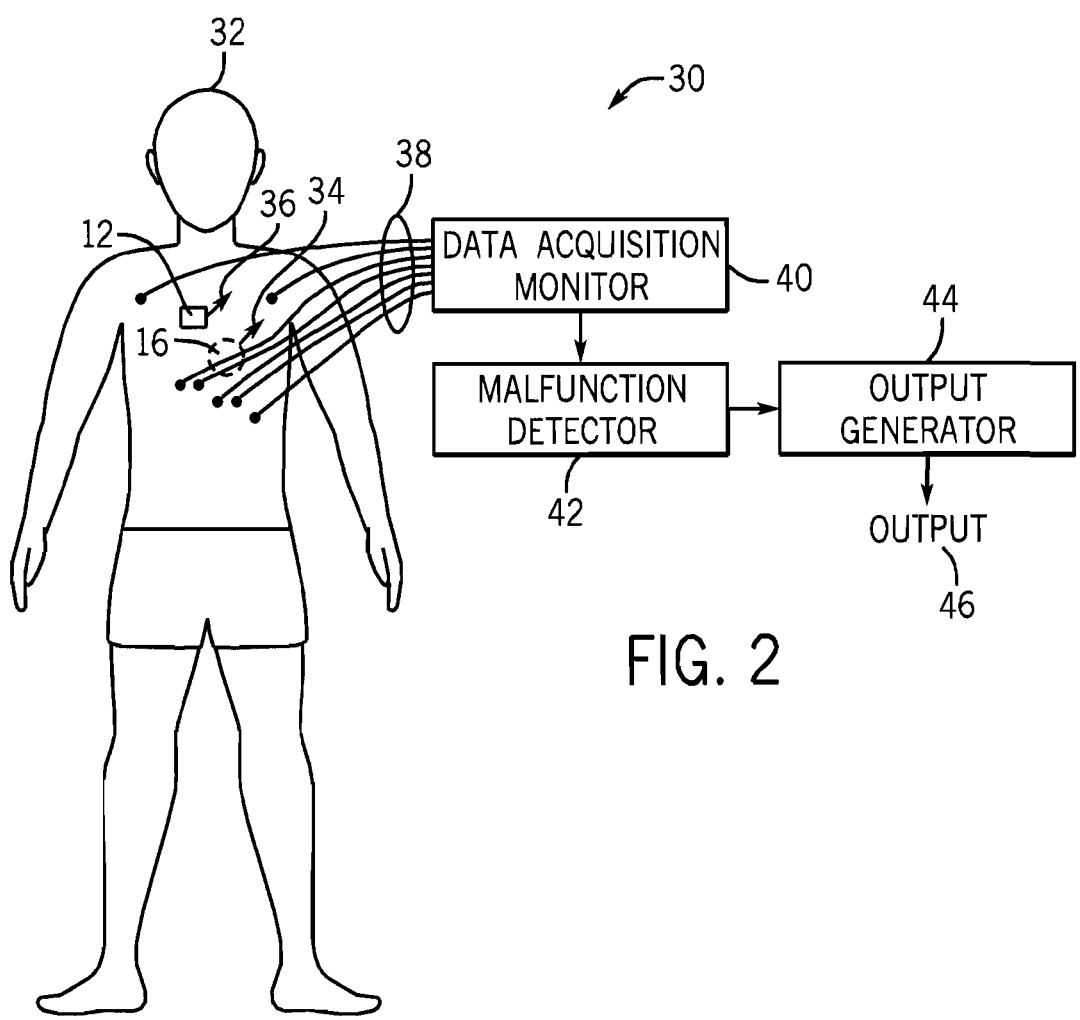
FIG. 2 depicts a system diagram of an embodiment of a system for detecting pacing system malfunctions.

FIG. 2 is a system diagram of a pacing system 30 with the ability to detect pacing system malfunctions. It should be noted that the system diagram of FIG. 2 is exemplary in nature and is not necessarily intended to reflect proper proper physiological or anatomical placement of the components of the pacing system 30, as would be recognized by one skilled in the art. In the pacing system 30, a patient 32 is receiving pacing therapy from an implantable pacemaker 12 that monitors the biopotential signal 34 produced by the patient's heart 16. Upon detection of an abnormality in the biopotential signal 34 from the patient's heart 16, the pacemaker 12 produces a pacer signal 36 in the form of an electrical impulse that stimulates the heart tissue at one or more of the pacer electrodes (22, 24, 28) as depicted in FIG. 1.

An external electrode array 38 is attached to the skin of the patient 32 in such a manner as to sense any biopotential signals 34 produced by the heart 16 of the patient 32 and pacing signals 36 produced by the pacemaker 12. The electrode array 38 receives a combined signal that includes the biopotential signal 34 and the pacer signal 36 through the skin of the patient 32. Since the pacer signal 36 is an electrical signal applied to the patient's heart 16, the electrode array 38 will sense the pacing stimulus 36 in conjunction with the biopotential signal 34 produced by the heart 16. Thus, the combined signal sensed by the electrode array 38 includes both the biopotential signal 34 from the heart 16 as well as the pacer signal 36 from the pacemaker 12. The placement of the electrode array 38 on the patient 32 may be manipulated such that the biopotential signal 34 and the pacer signal 36 are maximized while other biopotential signals from other physiological systems of the patient 32 are minimized.

A data acquisition monitor 40 receives the combined signal sensed by the electrode array 38. In the presently disclosed embodiment, the data acquisition monitor 40 is an ECG monitor 40. The ECG monitor 40 receives the sensed combined signal and converts the signal from an analog signal into a digital one. In embodiments, the ECG monitor 40 is a high bandwidth ECG monitor, wherein the combined signal sensed by the electrode array 38 is digitized at a high sampling rate in comparison to standard ECG monitoring techniques. Standard ECG monitoring techniques typically implement a digitizing sampling rate between 500 and 1000 Hz. In a high bandwidth and 1000 Hz. In a high bandwidth ECG monitor 40, the combined signal is sampled at a rate of 50 kHz or higher. The combined signal may be sampled at a rate between 50-75 kHz. Alternatively, the combined signal may be sampled at a rate higher than standard ECG monitoring techniques but at a rate below the disclosed high bandwidth ECG monitoring technique. These alternative sampling rates may be any sampling rate above 1 kHz and below 50 kHz. In some embodiments the high bandwidth of the combined signal provides increased signal data that facilitates the signal processing as described in further detail herein. The digitized ECG data is then provided to a malfunction detector 42.

The malfunction detector 42 receives the digitized combined signal data from the ECG monitor 40 and applies one or more algorithms or logic-based evaluations to the ECG data in order to determine the existence of a pacemaker malfunction. An embodiment of the malfunction detector 42 will be described in further detail with respect to FIG. 3 below. The malfunction detector 42 provides an indication of the detected pacemaker malfunction to an output generator 44. The output generator 44 receives the indication of the detected malfunction and produces an output 46 that is indicative of the detected malfunction. The output generator 44, in some embodiments, may be a graphical display connected to a computer workstation, the malfunction detector 42, or a hand-held computing device. The output 46 produced by the output generator 44 may be some type of visual output that notifies a clinician of the detected malfunction. The output 46 provided by the output generator 44 may be a textual output displayed on the monitor or graphical display of a computing system (not depicted) or a computer printout. The output 46 may also include the activation of an LED associated with a particular malfunction, or a digital output sent to an output generator 44 such as a remote electronic device including a PDA, cell phone, or laptop computer using such communication platforms such as email or SMS.

Figure 3:
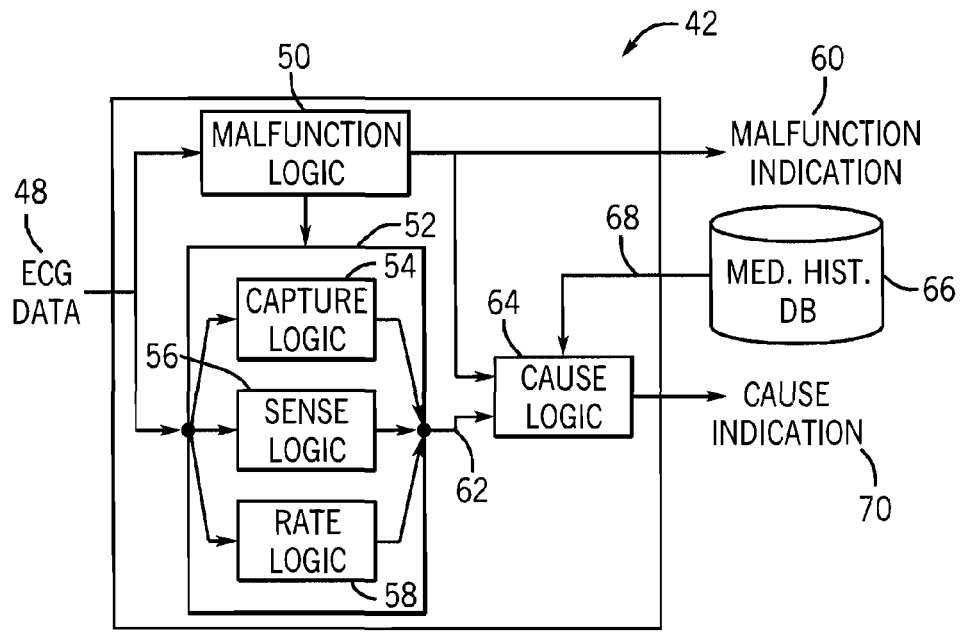
FIG. 3 depicts a more detailed embodiment of a portion of the system for detecting pacing system malfunctions.

FIG. 3 depicts a more detailed embodiment of the malfunction detector 42. The malfunction detector 42 receives the combined signal 48 from the ECG ECG monitor 40. In the presently described embodiment, the combined signal 48 includes biopotential (ECG) signal data and pacer signal data. The combined signal 48 goes to malfunction logic 50 and morphology logic 52. The malfunction logic 50 receives the combined signal 48 and applies one or more algorithms, logical statements, or other signal processing techniques to identify a morphology that is representative of the biopotential signal in the combined signal 48 collected from the patient. The malfunction logic 50 may use pulse matching, time interval measurements, or fuzzy logic in order to identify any pacing system malfunctions.

Features that are characteristic of a particular malfunction may be used to determine whether the pacing system is experiencing a failure to sense, a failure to capture, or an inappropriate rate. A failure to sense malfunction may be detected when a pace pulse of the pacer signal is generated out of sync with the intrinsic rhythm of the ECG signal. A failure to capture malfunction may be identified by missing p-waves, escape beats, wide QRS complexes, or the appearance of the underlying rhythm abnormality in the ECG signal. Finally, an inappropriate rate malfunction may be identified based upon a higher than programmed pacemaker output in the pacer signal or missing p-waves, missing ventricular beats, or AV disassociation in the ECG signal. The identified pacing system malfunction from the malfunction logic 50 is provided to the morphology logic 52.

In order to identify a morphology of the combined signal 48 that is indicative of the cause of the pacing system malfunction, the combined signal 48 is provided to the morphology logic 52 wherein the combined signal 48 is processed by one or more of a capture logic 54, sense logic 56, or rate logic 58. The logic used to process the combined signal 48 may be selected based upon the pacing system malfunction identified by the malfunction logic 50.

The morphology logic 52 processes the combined signal 48 in order to identify one or more morphological features that would be indicative of the cause of the pacing system malfunction as identified by the malfunction logic 50. An exemplary list of the morphologies that may be identified includes areas of ECG data discontinuity discontinuity or artifact detection in the ECG signal or excessive pace droop or low pace amplitude in the pacer signal.

The malfunction indication 60 from the malfunction logic 50 and the identified morphology 62 from the morphology logic 52 are provided to the cause logic 64. The cause logic 64 may include boolean logic, fuzzy logic, or a decision tree, a neural network, or other algorithm based techniques for analyzing the malfunction indication 60 and the morphology indication 62 in order to determine a cause of the identified malfunction. In some instances, the cause logic 64 may require a comparison between a presently acquired combined signal, wherein there is a presumed malfunction, versus a normal, standardized, or previously acquired combined signal that is presumed to be normal and used as a baseline for the comparison. This historical medical information may be acquired from a medical history database 66 that is a part of the malfunction detector 42 or is communicatively connected to the malfunction detector 42. In alternative embodiments, other patient medical history information may be used in the determination of the cause of the detected malfunction. This other patient medical history may include the presence of a particular patient diagnosis, drug therapy, or measured physiological parameter.

The cause logic 64 analyzes the malfunction indication 60 and the morphology indication 62 and optional baseline medical data 68, to produce a cause indication 70. The cause indication 70 may indicate the cause of the detected pacing system malfunction as determined by the cause logic 64. The malfunction indication 60 and the cause indication 70 are then both provided to the output generator 44 depicted in FIG. 2.

In an alternative embodiment, the morphology logic 52 includes a capture logic 54, a sense logic 56, and rate logic 58 that not only identify a morphology of the combined signal to identify the cause of a pacing system malfunction, but each of these logics also include the necessary logic and/or algorithms to identify whether or not each of a failure to capture, failure to sense, or inappropriate rate pacing system malfunction has occurred. Thus, the malfunction detector 42 may be simplified wherein detector 42 may be simplified wherein the morphology logic 52 provides both the functions associated with the malfunction logic 50 and the morphology logic 52 as described with respect to FIG. 3.

Figure 4:
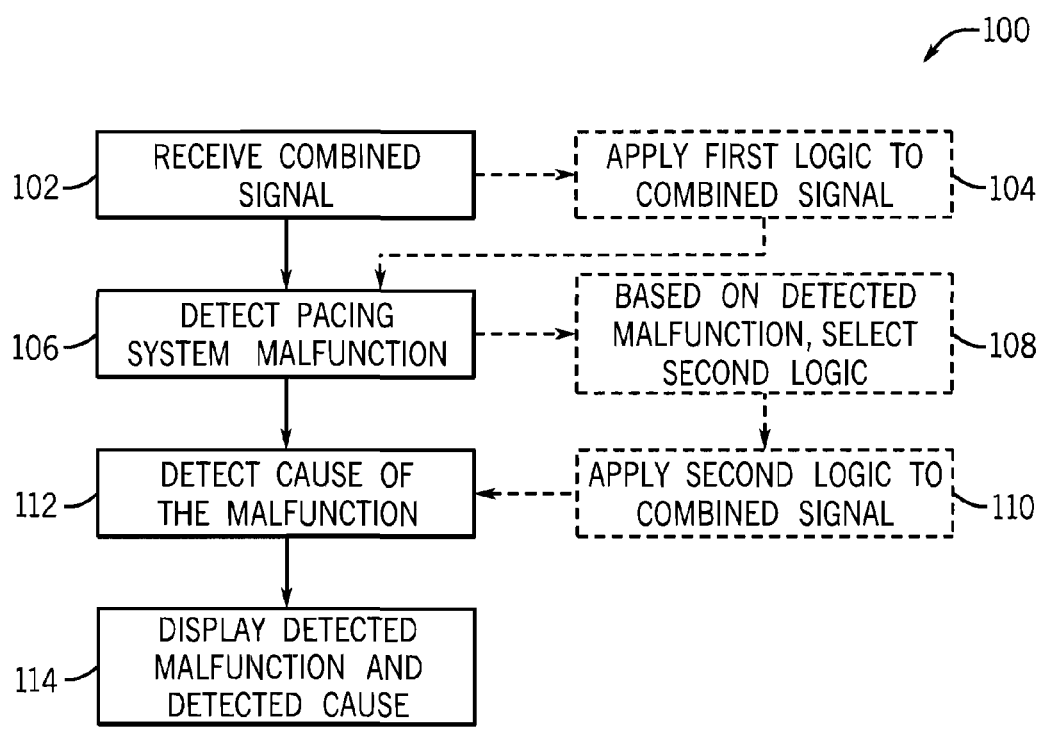
FIG. 4 is a flow chart depicting the steps of an embodiment of a method of diagnosing a malfunction of a pacing system.

FIG. 4 is a flow chart depicting the steps of an embodiment of a method of diagnosing a malfunction of a pacing system. First, a combined signal is received in step 102. The received combined signal includes an ECG signal and a pacer signal acquired from the skin of a patient. More specifically, the combined signal and/or the ECG signal may be digitized to be a high bandwidth ECG signal.

Next, a pacing system malfunction is detected in step 106. The detection of the pacing system malfunction may be performed by analyzing the combined signal received in step 102. The analysis of the combined signal received in step 102 may be further performed using an optional step of applying a first logic to the combined signal at step 104. The first logic applied to the combined signal in step 104 includes signal processing and/or algorithmic analysis of the combined signal in order to detect the pacing system malfunction in step 106. The pacing system malfunction is detected in step 106, since certain pacing system malfunctions exhibit characteristics in the sensed biopotential signals from a patient being treated with a pacing system, as has been described in further detail above.

Next, the cause of the malfunction is detected in step 112. This step is performed by analyzing the one or more pacing system malfunctions that were detected in step 106. This may be performed by further analyzing the morphologies of the combined signal in light of the detected pacing system malfunction. This may also be performed by an analysis of the detected pacing system malfunctions as a single cause may result in a combination of distinct malfunctions.

Alternatively, additional steps 108 and 110 may be implemented between steps 106 and 112. In step 108, a second logic is selected based upon the detected pacing system malfunction from step 106. The selected second logic may be tailored to analyze the combined signal to identify the cause of the malfunction once it has been determined. In step 110 the selected second logic is then applied to the combined signal and the cause of the malfunction is detected in step 112.

Finally, after the cause of the malfunction has been detected in step 112, the detected malfunction and the detected cause of the malfunction are displayed in step 114 such that the patient or an attending clinician is notified of the resulting analysis.

Figure 5:
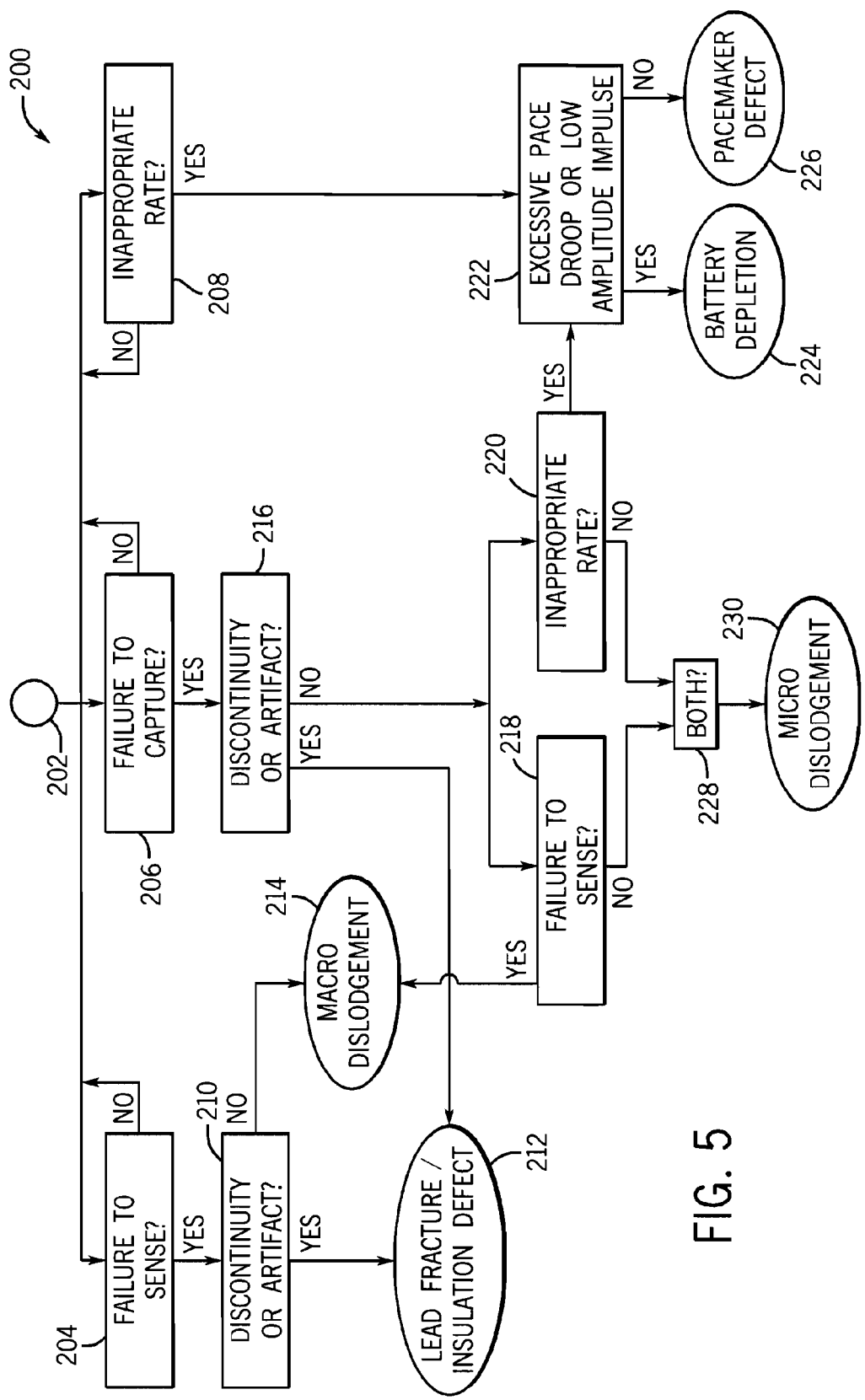
FIG. 5 is a flow chart depicting a more detailed alternative embodiment of a method of diagnosing a malfunction of a pacing system.

FIG. 5 is a flow chart of a more detailed embodiment of a method 200 of diagnosing a malfunction of a pacing system.

Additionally, FIG. 5 depicts an embodiment of a method that may be performed by malfunction detector 42 as depicted in FIGS. 2 and 3 and described above. The method 200 begins at node 202 where a combined signal is received from a patient that is being treated with a pacing system. The combined signal may be received via an ECG monitoring device, which in one embodiment is a high bandwidth ECG monitoring device. The combined signal at node 202 is analyzed to determine what, if any, pacing system malfunctions are present. This is done by blocks 204, 206, and 208 which respectively discern whether or not the biopotential signal exhibits a failure to sense 204, failure to capture 206, or an inappropriate rate 208 pacing system malfunction. This analysis may be performed in series or in parallel. If the analysis is performed in series, if one malfunction is not detected, the method moves to the other potential malfunctions for analysis.

Beginning with block 204, if a failure to sense is detected, then the combined signal is analyzed in block 210 to determine whether or not the signal exhibits any discontinuities or artifacts. The detection of a presence of a discontinuity or artifact in block 210 is indicative that the cause of the failure to sense detected in step 204 is a lead fracture or an insulation defect 212. If no discontinuity or artifact is detected in step 210, then the cause of the failure to sense is determined to be a macro dislodgement 214.

Next, at step 206 the combined signal is analyzed to determine whether or not the pacing system has a failure to capture malfunction. If such a failure to capture malfunction is detected in the combined signal, the signal is analyzed at step 216 analyzed at step 216 to determine if the signal exhibits a discontinuity or an artifact. Like with a detected failure to sense malfunction, if a discontinuity or artifact is identified in step 216, the cause of the failure to capture is determined to be a lead fracture or insulation defect 212.

If, however, the combined signal does not exhibit a discontinuity or artifact in step 216, the combined signal is further analyzed in steps 218 and 220. In step 218 the combined signal is analyzed to determine if a failure to sense malfunction is present. If the failure to sense malfunction is present in the pacing system, it is determined that the cause of both the failure to capture and failure to sense malfunctions is that of a macro dislodgement 214 in the pacing system. In step 220 the combined signal is analyzed to determine whether or not the pacing system is experiencing an inappropriate rate malfunction. If it is determined that the pacing system does exhibit an inappropriate rate malfunction, the combined signal is further analyzed in step 222 to determine whether the biopotential signal exhibits excessive pace droop or a low impulse amplitude. The determination in step 222 may require a previously acquired biopotential signal that is indicative of the pacing system properly operating under known operation conditions as the determination of the existence of excessive pace droop or low impulse amplitude in step 222 may require a serial analysis of a normal signal and the signal being analyzed. If the combined signal does exhibit excessive pace droop then it may be determined that the cause of the failure to capture and the inappropriate rate is due to the depletion of the pacemaker battery 224. If, however, the combined signal does not exhibit an excessive pace droop or a low impulse amplitude in step 222, then it may be determined that the cause of the failure to capture and inappropriate rate is that of a pacemaker software defect 226.

If, in steps 218 and 220 it is determined that the biopotential signal does not exhibit either a failure to sense malfunction or an inappropriate rate malfunction, then in step 228 it may be determined that only a failure to capture malfunction exists, while the sensing and the impulse rate of the pacing system are acceptable. In this situation, it may then be determined that the failure to capture malfunction is due to a micro dislodgement 230 of one or more of the pacer electrodes.

As disclosed above, an external source of additional patient information may be used to further supplement the determined malfunction and the ECG morphology. In these embodiments, information regarding the patient's underlying medical condition, concurrent drug treatments, or other recorded patient physiological parameters are used to supplement the received biopotential signal. One example of a determination that may be facilitated by the inclusion of additional patient information would be that of a failure to capture that is due to metabolic abnormalities in the patient, since metabolic abnormalities may have an effect on the pacing of the heart by affecting the propagation of electrical impulses through the heart tissue.

Embodiments of the presently disclosed system and method exhibit the advantage of diagnosing a pacing system malfunction through the use of surface ECG. The process for acquiring a surface ECG is well known to many clinicians and often the required technology is readily available in many clinical settings. The same is not true for tools typically used to diagnose pacing system malfunctions prior to this invention. Chest X-rays that are costly and time consuming are used to detect lead dislodgments and specialized RF devices that communicate with an implanted pacemaker can receive signals indicative of pacemaker function. However, these tools are not always readily available to the clinician and require specialized skills that most clinicians do not possess. The presently disclosed system and method can provide the clinician with a fast and economical diagnosis of a pacing system malfunction. This diagnosis may then allow the clinician to use the other identified techniques to confirm the diagnosis, or the clinician may be directed to a particular technique that is preferred for confirming the diagnosed pacing system malfunction.

It should be noted that some embodiments of the system and method as disclosed herein may be implemented solely through the use of a computer. In such embodiments, computer code stored on a computer readable medium may be used to form functional segments that carry out the functions of the elements of an embodiment of the system, or carry out the steps of an embodiment of the method when executed by one or more microprocessors or general purpose or specific purpose computer controllers. The technical effect of such an embodiment the system or method would be to provide a clinician with an analysis not only of the type of pacing system malfunction, but also an analysis of the root cause of that pacing system malfunction all while subjecting the patient to non-invasive or minimally invasive data collection techniques.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent elements with insubstantial differences form the literal languages of the claims.

What is claimed is:

1. A method of diagnosing a malfunction of a pacing system, comprising the steps of:
   receiving a combined signal that is a high bandwidth combined signal that comprises a biopotential signal and a pacer signal;
   applying a first logic to the high bandwidth combined signal, the first logic being directed to detecting a pacing system malfunction when applied to the high bandwidth combined signal;
   detecting a pacing system malfunction;
   determining a cause of the detected malfunction; and
   displaying the detected malfunction and the determined cause of the malfunction.

2. The method of claim 1, further comprising the steps of:
   selecting a second logic based on the detected pacing system malfunction; and
   applying the second logic to the high bandwidth combined signal.

3. The method of claim 2, wherein the second logic is a morphology-based logic, that determines a cause of the detected malfunction based on the morphology of the high bandwidth combined signal.

4. The method of claim 1 wherein the detected pacing system malfunction is an inappropriate rate, and the determined cause of the malfunction is a pacemaker defect.

5. A method of diagnosing a malfunction of a pacing system, the method comprising the steps of:
   receiving a combined signal;
   detecting a pacing system malfunction;
   selecting a morphology logic to apply to the combined signal to determine the cause of the detected malfunction; and
   identifying a morphological feature of the combined signal based on the application of the morphology logic to the combined signal;
   determining a cause of the detected malfunction; and
   displaying the malfunction and the determined cause of the malfunction;
   wherein the step of detecting a pacing system malfunction detects a failure to sense malfunction, the morphology logic is selected based upon the detected failure to sense malfunction, and the determined cause of the malfunction is lead fracture.

6. The method of claim 5, wherein the received combined signal is a high bandwidth signal and further comprises a biopotential signal and a pacer signal.

7. A method of diagnosing a malfunction of a pacing system, the method comprising the steps of:
   receiving a combined signal;
   detecting a failure to capture pacing system malfunction;
   detecting a failure to sense pacing system malfunction;
   based upon the detected failure to capture and the detected failure to sense malfunctions, determining a macro dislodgement cause of the failure to capture and failure to sense pacing system malfunctions; and
   displaying the detected malfunction and the determined cause of the malfunction.

8. The method of claim 7, wherein the received combined signal is a high bandwidth signal and further comprises a biopotential signal and a pacer signal.

9. A method of diagnosing a malfunction of a pacing system, the method comprising the steps of:
   receiving a combined signal;
   detecting a pacing system malfunction;
   determining a cause of the detected malfunction; and
   displaying the detected malfunction and the determined cause of the malfunction;
   wherein the detected pacing system malfunction is a failure to capture, and the determined cause of the malfunction is micro dislodgement.

10. The method of claim 9 wherein the detected failure to capture pacing system malfunction is detected in the absence of the detection of a failure to sense and an inappropriate rate pacing system malfunctions.

11. The method of claim 9, wherein the received combined signal is a high bandwidth signal and further comprises a biopotential signal and a pacer signal.

12. A method of diagnosing a malfunction of a pacing system, the method comprising the steps of:
   receiving a combined signal;
   detecting an inappropriate rate pacing system malfunction;
   detecting a failure to capture pacing system malfunction;
   selecting a logic to apply to the biopotential signal based on the detected inappropriate rate and failure to capture pacing system malfunctions;
   applying the selected logic to the biopotential signal;
   identifying an excessive pace droop biopotential signal morphology;
   determining a cause of the detected malfunction; and
   displaying the detected malfunction and the determined cause of the malfunction;
   wherein the determined cause of the malfunction is depletion of a pacing system battery.

13. The method of claim 12, wherein the received combined signal is a high bandwidth signal and further comprises a biopotential signal and a power signal.

14. A system for detecting pacing system malfunctions, the system comprising:
   an electrode array configured to be attached to a patient being treated with an electrical pacing system, the electrode array receiving a combined signal comprising a signal associated with the electrical pacing system and a biopotential signal;
   a malfunction detector, the malfunction detector comprising a malfunction logic and a morphology logic, the malfunction detector receiving the combined signal, applying the malfunction logic to the combined signal to identify a pacing system malfunction, and applying the morphology logic to the combined signal to identify a morphology of the combined signal, the morphology being indicative of the cause of the malfunction; and
   an output generator connected to the malfunction detector, the output generator receiving an indication of the identified pacing system malfunction and the identified cause of the malfunction, the output generator creating an output that displays the identified pacing system malfunction and the identified cause.

15. The system of claim 14 further comprising an ECG monitor that collects the combined signal from the electrode array.

16. The system of claim 15 wherein the combined signal collected by the ECG monitor is a high bandwidth combined signal.

17. The system of claim 16 further comprising a cause logic that receives the identified pacing system malfunction from the malfunction logic and receives the identified morphology of the combined signal, the cause logic determining the cause of the malfunction based upon the identified malfunction and the identified morphology.

18. The system of claim 17 further comprising a medical history database, the medical history database comprising historical patient data, the medical history database being connected to the cause logic such that the cause logic is provided with patient medical history data and the cause logic compares the morphology of the combined signal with a morphology of a previously acquired combined signal.

19. A pacing system comprising:
   a pacemaker connected to the heart of a patient, the pacemaker periodically stimulating the heart;
   an electrode array attached to the patient at locations suitable for acquisition of a combined signal including a biopotential signal from the heart and a pacer signal from the pacemaker;
   an ECG monitor connected to the electrode array, the combined signal acquired by the electrode array being transmitted to the ECG monitor;
   a malfunction detector applying a malfunction logic to the acquired combined signal, the malfunction logic identifying at least one pacing defect present in the combined signal and applying a morphology logic to the combined signal to identify a morphology of the combined signal, the morphology of the combined signal being indicative of a cause of the at least one pacing defect; and
   an output generator connected to the malfunction detector, the output generator receiving an indication of the determined cause of the malfunction and producing an output indicative of the determined cause.

20. The system of claim 19 further comprising a cause logic that receives the identified at least one pacing defect from the malfunction logic and the identified morphology from the morphology logic, the cause logic determining a cause of the at least one pacing defect.

21. The system of claim 20 wherein the morphology logic comprises a plurality of morphology logics, a logic applied to the combined signal being selected from the plurality of morphology logics based upon the identified at least one pacing defect.

22. The system of claim 20 further comprising a medical history database, the medical history database comprising additional patient information; the cause logic receiving the additional patient information from the medical history database and determining the cause of the at least one pacing defect based upon the identified at least one pacing defect, the identified morphology, and the additional patient information.

* * * * *